(12) United States Patent
Koullick et al.

(10) Patent No.: US 10,064,981 B2
(45) Date of Patent: Sep. 4, 2018

(54) CATHETER WITH DRUG COATING

(71) Applicant: BAYER PHARMA AKTIENGESELLSCHAFT, Berlin (DE)

(72) Inventors: Edouard A. Koullick, Golden Valley, MN (US); Richard F. Murphy, White Bear Lake, MN (US); Jonathan Schmidt, Maple Grove, MN (US)

(73) Assignee: Bayer Pharma Aktiengesellschaft, Berlin (DE)

( * ) Notice: Subject to any disclaimer, the term of this patent is extended or adjusted under 35 U.S.C. 154(b) by 97 days.

(21) Appl. No.: 14/413,378

(22) PCT Filed: Jul. 10, 2013

(86) PCT No.: PCT/US2013/049973
§ 371 (c)(1),
(2) Date: Jan. 7, 2015

(87) PCT Pub. No.: WO2014/011805
PCT Pub. Date: Jan. 16, 2014

(65) Prior Publication Data
US 2015/0231308 A1    Aug. 20, 2015

Related U.S. Application Data

(60) Provisional application No. 61/669,831, filed on Jul. 10, 2012.

(51) Int. Cl.
*A61L 29/08* (2006.01)
*A61L 29/16* (2006.01)
*A61M 25/10* (2013.01)

(52) U.S. Cl.
CPC ........... *A61L 29/16* (2013.01); *A61L 29/08* (2013.01); *A61M 25/10* (2013.01); *A61M 25/1027* (2013.01); *A61L 2420/02* (2013.01); *A61L 2420/06* (2013.01); *A61M 2025/105* (2013.01)

(58) Field of Classification Search
CPC ........ A61L 29/085; A61L 29/16; A61L 29/08; A61L 2420/02; A61L 2420/06; A61M 25/10; A61M 25/1027; A61M 25/1038; A61M 2025/1031; A61M 2025/105
See application file for complete search history.

(56) References Cited

U.S. PATENT DOCUMENTS

| | | | | |
|---|---|---|---|---|
| 6,126,652 A | * | 10/2000 | McLeod | A61M 25/1038 606/1 |
| 2003/0215564 A1 | * | 11/2003 | Heller | A61F 2/86 427/2.25 |
| 2007/0196423 A1 | * | 8/2007 | Ruane | A61L 31/10 424/423 |

(Continued)

OTHER PUBLICATIONS

PCT/US2013/049973, The International Search Report and The Written Opinion of the International Searching Authority, dated Oct. 2, 2013.

(Continued)

*Primary Examiner* — Nathan R Price
*Assistant Examiner* — Justin L Zamory

(57) ABSTRACT

A composition and methods for improved delivery of a therapeutic agent to a stenosed vessel wall.

10 Claims, 2 Drawing Sheets

(56) References Cited

U.S. PATENT DOCUMENTS

| | | | |
|---|---|---|---|
| 2008/0255510 A1* | 10/2008 | Wang | A61K 31/337 |
| | | | 604/103.02 |
| 2010/0228228 A1 | 9/2010 | Speck et al. | |
| 2010/0278997 A1 | 11/2010 | Speck et al. | |
| 2011/0099789 A1* | 5/2011 | Ewing | A61M 25/1002 |
| | | | 29/428 |
| 2011/0238011 A1 | 9/2011 | Scheller et al. | |
| 2011/0295200 A1* | 12/2011 | Speck | A61L 29/06 |
| | | | 604/103.02 |

OTHER PUBLICATIONS

PCT/US2013/049973, International Preliminary Report on Patentability, dated Jan. 22, 2015.

Bodo Cremers et al. "Comparison of two different paclitazel-coated Balloon Catheters in the Porcine Coronary Restenosis Model," Clinical Research in Cardiology, Steinkopff-Verlag, Da, col. 98, No. 5, Mar. 12, 2009, pp. 325-330.

* cited by examiner

CATHETER WITH DRUG COATING

RELATED APPLICATION

The present application claims priority to U.S. Provisional Patent Application No. 61/669,831, filed on Jul. 10, 2012, which is incorporated herein by reference.

FIELD OF THE DISCLOSURE

Embodiments of the present disclosure generally relate to coated medical devices and methods for coating medical devices. More particularly, embodiments of the present disclosure relate to percutaneous transluminal angioplasty balloon catheters coated with a therapeutic agent and methods for coating percutaneous transluminal angioplasty catheter balloons.

BACKGROUND

The following background information is provided to assist the reader to understand embodiments disclosed below and the environment in which they may be used. The terms used herein are not intended to be limited to any particular narrow interpretation unless clearly stated otherwise, either expressly or impliedly, in this document.

Medical devices, such as percutaneous transluminal angioplasty (PTA) balloon catheters, are often coated with various agents, including for example therapeutic agents, radiopaque materials, lubricious materials, hydrophilic materials, and biocompatible materials. PTA is a medical procedure that is used to reduce or eliminate blockages within the vascular system in order to relieve clinical symptoms associated with reduced blood flow to an organ or region of the body. PTA works by placing a non-elastomeric balloon within a blockage or narrowing and inflating it with sufficient force to restore blood flow to the distal anatomy. The balloon both compresses and expands the atherosclerotic plaque to effectively enlarge a previously constricted lumen. This procedure has become a primary therapy for treatment of occlusive vascular disease.

Unfortunately, PTA has a very high incidence of restenosis, sometimes exceeding 50%. In some circumstances, a bare metal stent (BMS) or a drug eluting stent (DES) is placed at the site of the plaque after PTA to prevent restenosis. A BMS reduces the incidence of restenosis to approximately 20% and although DES's are not currently approved for the peripheral arteries, a DES can reduce restenosis to less than 5% in the coronary arteries. While a DES is the preferred method of treatment of occlusive vascular disease (OVD) in the coronary arteries currently, problems related to late restenosis and late in-stent thrombosis have been noted with DES. In addition, the patient must remain on antiplatelet and anticoagulant therapy for an extended period of time after the procedure. Therefore, there is a need for alternate or improved therapies for the treatment of OVD. Recent therapies involve the use of drug coated PTA catheter balloons, with or without a bare metal stent, for the delivery of the drug at the lesion site to prevent restenosis.

Standard methods for coating PTA catheter balloons, such as dip coating, have several drawbacks. For example, the coating is inconsistent, non-uniform, and shreds away during handling. In addition, the process is very labor intensive, lengthy, and environmentally unfriendly. Thus, there is a continued need for improved PTA catheter balloons and methods of coating catheter balloons providing uniform and consistent delivery of effective dosages of therapeutic agents to target locations with reduced systemic dosages as well as reduced manufacturing costs.

SUMMARY

In general, various embodiments of the disclosure are directed to methods for optimizing coating of medical devices, such as balloon catheters, including metered and consistent concentrations of therapeutic agents. Various embodiments of the present disclosure are also directed to catheter balloons and PTA catheters with optimized coating features.

In one embodiment, the present disclosure provides a method of making a balloon catheter, the method comprising: providing a balloon catheter comprising a catheter having a balloon coupled to one end of the catheter, wherein the balloon has an external surface, a length, and a circumference; providing a coating solution; and coating the balloon with the coating solution and drying the coating solution on the balloon to provide a balloon catheter having a dried coating on the external surface of the balloon. In this embodiment, the coating solution includes: 30 mg/ml to 90 mg/ml paclitaxel; at least 45 mg/ml iopromide; 7.5 vol-% to 50 vol-% acetone; 30 vol-% to 80 vol-% ethanol; and at least 4 vol-% water.

In another embodiment, the present disclosure provides a method of coating a folded balloon catheter, the method comprising: providing a balloon catheter comprising a catheter having a folded balloon coupled to one end of the catheter, wherein the balloon has an external surface, a length, and a circumference; immersing the folded balloon in a pre-conditioning solution; at least partially drying the pre-conditioning solution on the balloon to form a pre-conditioned balloon; partially expanding the pre-conditioned balloon; and coating the external surface of the pre-conditioned balloon with a restenosis inhibitor.

In yet another embodiment, the present disclosure provides a method of coating a balloon catheter comprising: providing a balloon catheter comprising a catheter having a folded balloon coupled to one end of the catheter; subjecting the folded balloon to a pre-conditioning cycle to form a pre-conditioned balloon; partially inflating the balloon (before or after subjecting the balloon to the pre-conditioning cycle); coating the pre-conditioned and partially inflated balloon with a coating solution comprising a restenosis inhibitor; wherein the coating step comprises applying a predetermined amount of the coating solution at a flow rate of 0.2 µl/sec to 6 µl/sec while the balloon is being rotated; and drying the coating solution to form a dried coated balloon coupled to the catheter, wherein the dried coating comprises the restenosis inhibitor.

The present disclosure also provides balloon catheters prepared by the methods of the present disclosure.

In one embodiment, a balloon catheter includes a catheter having a balloon coupled to one end of the catheter, wherein the balloon has an external surface, a length, and a circumference; wherein the external surface of the balloon is coated with a dried coating comprising a restenosis inhibitor; wherein the coating is a uniform coating with +/−15% variation along the length and around the circumference of the balloon; wherein the coating is a conformal coating with a thickness ranging from 2 µm to 20 µm; and wherein the dried coated balloon releases less than 30 particulates of the dried coating per $mm^2$ of the balloon surface during expansion of the coated balloon.

The present disclosure also provides methods of treating a vessel wall. For example, in one embodiment, the method includes: positioning a balloon catheter of the present disclosure in a stenosed vessel of a subject; inflating the balloon of the balloon catheter to an expanded configuration, wherein the vessel wall of the stenosed vessel is in physical communication with a substantial portion of the external surface of the balloon when inflated; and transferring paclitaxel and iopromide to the vessel wall from the external surface of the balloon.

In another embodiment, the method includes: positioning a balloon catheter of the present disclosure in a stenosed vessel of a subject; inflating the balloon of the balloon catheter to an expanded configuration, wherein the vessel wall of the stenosed vessel is in physical communication with a substantial portion of the external surface of the balloon when inflated; transferring a restenosis inhibitor to the vessel wall from the external surface of the balloon; and maintaining contact between the external surface of the balloon and the vessel wall for a time sufficient to deliver a therapeutically effective amount of the restenosis inhibitor to a treatment site of the stenosed vessel.

Those and other details and advantages of the present disclosure will become better understood or apparent from the following description and drawings showing embodiments thereof.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one."

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise. The term "and/or" means one or all of the listed elements or a combination of any two or more of the listed elements.

Also herein, unless otherwise specified, all numbers assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.). Herein, "up to" a number (e.g., up to 50) includes the number (e.g., 50).

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DESCRIPTION

Figure 1:
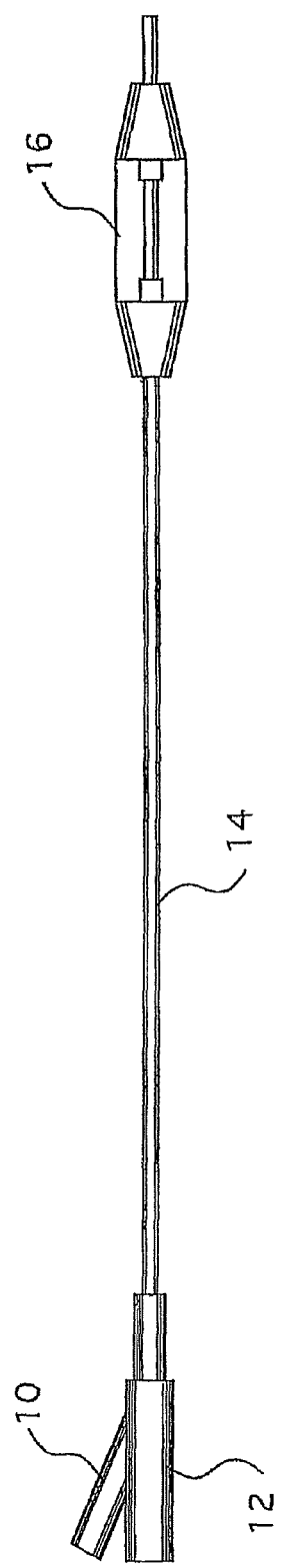
FIG. 1 is a general schematic diagram of a PTA balloon catheter.

In all of its embodiments and related aspects, the present disclosure may be used with medical devices, including, but not limited to, for example, PTA balloon catheters. Other examples of medical devices include, without limitation, drainage catheters, replacement or artificial venous valves, aortic valves, replacement valves, ventricular catheters, ventriculostomy balloons, balloon expandable stents, and coronary balloons.

Medical devices are routinely coated with compositions including, for example and without limitation, therapeutic agents, radiopaque materials, radioactive materials, polymeric materials, sugars, waxes, fats, and lubricious materials. As used herein, "therapeutic agent" includes, but is not limited to, any therapeutic, for example drugs, genetic material, and biological material. Genetic material includes for example, without limitation, DNA or RNA, viral vectors and non-viral vectors. Biological material includes for example, without limitation, cells, bacteria, proteins such as growth factors, peptides, lipids, and hormones. Drugs include, without limitation, anti-thrombogenic agents, anti-proliferative agents, anti-inflammatory agents, anti-neoplastic agents such as epothilone and its derivatives, antimiotic agents, antioxidants, anti-coagulants, immunosuppressants such as sirolimus and its derivatives, vascular cell growth promoters, vascular cell growth inhibitors, antibiotic agents, angiogenic substances, restenosis-inhibiting agents, and drugs for heart failure. The "active agent" or "therapeutic agent" may include a combination of one or more therapeutics. Particular embodiments include restenosis-inhibiting agents such as Taxol, paclitaxel, paclitaxel analogues, derivatives, and mixtures thereof. The coatings can be in solid, liquid, or gas forms depending on the method used to coat the device. In an example, carriers may be used with the therapeutic, such as, for example and without limitation, bioabsorbable agents, microspheres, microtubes, and physiologically compatible non-reactive drug transfer or radio opaque agents, such as urea, iopromide, cremophore EL, vitamin E, Tocopheryl Polyethylene Glycol Succinate (TPGS), and the like.

Various embodiments described herein pertain to a PTA catheter balloon that has a specialized coating containing a therapeutic agent. The PTA catheter balloon both dilates a stenotic lesion and simultaneously impregnates a therapeutic agent into the vascular wall during inflation. In another embodiment, the present disclosure is particularly useful in treatment of peripheral vascular disease in vessels with long, diffuse lesions, such as iliac, femoropopliteal, and tibial/below the knee arteries.

Peripheral vascular disease has several distinguishing characteristics from its coronary counterpart even though the underlying atherosclerotic process is similar. First, the peripheral vasculature can range in diameter from 12 mm for iliac to less than 2 mm for tibial arteries compared to coronary which can range from 1.5-4 mm. For most peripheral vascular disease, the lesions are longer and more diffuse whereas for coronary artery disease, they are shorter and more focal. Also, the location of the target arteries is more variable, resulting in different length catheters. In addition, stents are particularly problematic in peripheral vasculature due to stent fractures and low long term patency rates. Other applicable vasculatures include renal, which has a diameter of about 4-7 mm and a length of about 15-40 mm, and intracranial, which has a diameter of about 1-3 mm and a length of about 5-30 mm.

Embodiments of the present disclosure pertain to both over-the-wire and rapid exchange PTA catheters. FIG. 1 is a general schematic of a PTA catheter including, without limitation, an inflation lumen 10, a guidewire lumen 12, a shaft 14, and a balloon 16. Various embodiments of the present disclosure relate to methods for applying and adhering a coating containing a therapeutic agent to catheter balloon 16 used generally in all angioplasty procedures, including balloon expandable stents.

Various embodiments of the present disclosure pertain to an adherent coating containing a therapeutic agent on the balloon 16 for inhibiting restenosis after angioplasty. As an example, the coating is a blend of iopromide and paclitaxel dissolved in solvents to form a solution which is then applied to the balloon 16. Solvents include, for example and without limitation, methanol, ethanol, acetone, isopropanol, methyl ethyl ketone, ethyl acetate, butyl acetate, butyl chloride, chloroform, diethyl ether, dimethyl sulfoxide, dimethyl formamide, tetrahydrofuran, glycerin, essential oils, water, mixtures thereof, etc. For example, the target concentration average drug range for paclitaxel is 0.5-10.5 micrograms/mm$^2$ ($\mu$g/mm$^2$) of total balloon 16 surface area, more preferably about 2-6 $\mu$g/mm$^2$, and more preferably about 3±10% $\mu$g/mm$^2$. The coating is dynamically released upon inflation of the balloon 16 and transferred to a vessel wall (e.g., arterial wall). After deflation, the drug remains impregnated in arterial tissue to inhibit restenosis.

In an examplary embodiment, a coating that avoids a high number of particulates released during expansion of the coated balloon is preferred. Moreover, a coating that provides a high level of uniformity on the surface of the balloon is also preferred. Coating along the length of the balloon and also around the circumference of the balloon during manufacturing provides a uniform surface coating. However, the coating must also provide a favorable drug transfer to vessel walls with acceptable drug retention over time. In order to achieve the aforementioned coating characteristics, one example embodiment of a coating platform includes one or more of the following: a decreased level of particulates that is generated upon balloon expansion that is about ⅕th (or about 20%) of prior coating platforms particulate levels along with a minimization of the size of the particulates released upon balloon inflation. In addition, a coating that also improves the coating distribution on the balloon surface (i.e., a conformal and uniform coating+/−15% and preferably +/−10%) is preferred. Finally, the resulting coating has a high level of drug transfer to the vessel wall, while still maintaining a high level of retention to the balloon surface prior to delivery. This interplay between drug transfer and retention will maintain a high level of efficacy in the drug delivery to the vessel wall.

In certain embodiments, an active agent such as paclitaxel can be combined with a contrast agent (e.g., ULTRAVIST 370 contrast media from Bayer Schering Pharma AG that includes 75% Iopromide and about 25% water). The ULTRAVIST contrast media acts as the carrier or excipient to allow for active agent uptake into the vessel wall. The combination of an active agent such as paclitaxel and a contrast agent such as iopromide is referred to herein as a restenosis inhibitor.

An alternative coating formulation having higher levels of ULTRAVIST contrast media (75% Iopromide and about 25% water) than conventional coating formulations provide a near saturation level of Paclitaxel. In an examplary embodiment, a solution was found to be about 60 mg/ml Paclitaxel solubilized with an appropriate ethanol and acetone mixture. In another example embodiment, 30 mg/ml to 90 mg/ml Paclitaxel and 7.5% to 50% acetone are combined to make an active agent. A coating formulation manufactured to produce larger volumes to achieve the 3 $\mu$g/mm$^2$ drug loading can also be achieved within this and several related embodiments. The concentration of Paciltaxel described herein is markedly less than other coating formulations known in the art (i.e., 90 $\mu$g/ml). However, the reduced drug loading also provides a bioeffective amount of active agent (e.g., Paclitaxel). In this embodiment the distribution of crystalline Paclitaxel was reduced throughout the coating, but did transfer adequate amounts of bioavailable drug to the vessel wall to meet the drug transfer and retention requirement, while not sacrificing the uniformity and low particulate levels.

In certain embodiments, a coating solution can be prepared by weighing out paclitaxel (6000.0 mg per 100 ml coating solution); adding an amount of acetone (e.g., 40 ml) to dissolve the paclitaxel; using a Harvard Twin Syringe Pump to add 32.5 ml ethanol; sonicating the mixture for 10-15 minutes until the solution is homogeneous and clear; using the syringe pump, adding ULTRAVIST 370 ("UV370", 20.0 ml), which includes iopromide, water, and a preservative, to the solution of paclitaxel in ethanol and acetone; lightly agitating the solution until it is homogeneous and clear; bringing the solution to volume (100 ml) with acetone (often <10 ml); sonicating the mixture for 10-15 minutes until solution is homogeneous and clear; and allowing the solution to cool for approximately 5 minutes after ultrasonication. This provides a "final" coating solution that includes: 60 mg/ml paclitaxel; 154 mg/ml iopromide (20 ml UV370×769 mg Iopromide/1 ml UV370=15377.2 mg iopromide→in 100 ml total solution=154 mg/ml); 32.5 vol-% ethanol; 40 vol-% acetone; and 4.6% water (the source of water is UV370, which has 769 mg/ml of Iopromide, therefore 231 mg/ml H$_2$O→(231 mg×20 ml UV370)/(1000 mg/1 g)=4.62 g=4.62 ml/100 ml total solution× 100%=4.6% water).

Thus, in certain embodiments, a coated medical device is provided that includes: a catheter, extending along a longitudinal axis and having a first end and a second end and having at least one lumen; a balloon coupled to said first end or said second end; a coating for delivery of a restenosis inhibitor, wherein said coating is a uniform coating on the external surface of a balloon catheter such that the restenosis inhibitor is at a concentration of about 3 µg/mm$^2$ and said coating is provided by a coating solution having 7.5 vol-% to 50 vol-% acetone, 30 vol-% to 80 vol-% ethanol, 30 mg/ml to 90 mg/ml Paclitaxel, at least 45 mg/ml iopromide, and at least 4.0% water (or at least 10% water, or at least 40% water, and often no more than 40% water).

In an optional step to further improve uniformity, and reduce a very rapid wetability/migration issue, the coating can be dispensed on the surface of the balloon in a relatively rapid manner. Selecting parameters that would quickly apply the drug coating onto the balloon to allow the entire solution to be "painted" onto the surface of the balloon without any part of the coating becoming completely dry is preferred.

Embodiments of the invention include methods for coating a catheter balloon. The coated balloon may be manufactured using a metered dispensing process to precisely "paint" or dispense the coating solution on the balloon surface. The coated balloon may then be placed into a balloon protective sheath while the coating has not completely dried as the coating continues to dry after being sheathed. Alternatively, the coating may be dry before being placed into a protective sheath. Exemplary specifically-sized protective sheaths for a given balloon diameter are disclosed in U.S. Patent Publication No. 2011/0099789 published on May 5, 2011 filed on May 1, 2009. The specifically-sized protective sheath can be placed over the balloon before or after coating of the balloon. The specifically-sized protective sheath can aid in metered methods of coating catheter balloons as well as coating distribution and protection.

In another embodiment, a balloon of a balloon catheter is coated with a coating solution as described herein. The coating is allowed to dry under prolonged parameters, which includes slower drying. In several related embodiments the coating dries fast enough to prevent migration, but dries slow enough to allow precipitation, crystallization and/or drug retention.

The coating may be applied to the surface of the balloon in a multiple layer format, such as a dual layer coating. The at least one subsequent coating layers may be applied in a number of various manners. In one particular embodiment, the at least one subsequent coating layer is directly overlain on the first coating layer. The at least one subsequent coating layer may be applied to the first coating layer once the first layer is completely dry. In an alternative embodiment, the at least one subsequent coating layer is applied to the first layer prior to the first layer being completely dry.

In another examplary embodiment, to further improve the reduced particulates levels of a drug delivery coating, a heat source such as an IR source can be used for rapid drying to improve uniformity along the length of the balloon. The use of a heating source should also take into account adequate drying time to prevent too rapid drying, because too rapid drying times can give poor biological performance. In one embodiment, where the heat source is included as a drying parameter, the particulate levels may also be decreased. A balance of rapid drying to provide a uniform coating and low levels of particulate formation upon balloon expansion, and slower drying to provide good biological performance, is desired. For certain embodiments 1-2 minutes drying time is suitable.

For example, in one exemplary embodiment, the balloon catheter is semi-inflated and a coating is applied via a single pass (e.g., using a syringe) onto the balloon. The coating on the balloon surface is dried rapidly, the dry coating is substantially transparent. Additionally, at least this embodiment is also characterized by having a high degree of uniformity and lower particulate count.

In another exemplary embodiment, the coating solution is a nearly saturated coating solution. Furthermore, the coating solution does not include the step of rapid drying with known drying methods such as IR heat.

In certain embodiments, the balloon catheter undergoes a pre-coating inflation process prior to the several above mentioned application techniques to achieve the uniformly distributed coating on the balloon surface. That is, the balloon is partially expanding the balloon, for example, by inflating to a pressure of 3 psi.

In certain embodiments, once the coating has completed a "drying" cycle, the pressure applied prior to coating (e.g., 3 psi) is released from within the balloon. In one example embodiment, a drying cycle of 180 second rotation after coating is used, the pressure within the balloon being released and an oversized first sheath (e.g., a PTFE pre-sheath) then being slid onto the balloon to reduce the diameter of the inflated balloon and aid the balloon to fold back onto itself. Once the oversized sheath is in place, vacuum (e.g., −5 psi) is applied to the balloon to a dimension that is reasonable for a second (final) sheath to be placed onto the coated balloon. The balloon will remain in this configuration until the balloon catheter is employed in a clinical setting. It should be appreciated the pre-sheath step is an important step in the coating process to keep the balloon from "pancaking" when the vacuum was applied. The resulting final sheath on the balloon retains less of the drug (0.6%) as compared to a sheath covering other conventionally coated balloons (3.1%) when removed from balloon. Although not wanting to be bound by a particular theory, the increased balloon retention of drug (versus drug transfer to interior lumen of the sheath) is probably related to the coating being substantially dry when the sheath is placed onto the balloon. In addition, the coating is considered to have more integrity since it has shown to retain more drug (i.e., active or therapeutic agent) on the balloon surface after being pushed through a typical introducer. In one particular embodiment, the coating retained 75% of the active agent compared to 34% of active agent using a conventional coating method that involves placement of a sheath onto a wet balloon.

Although several modifications to enhance drug delivery efficacy are within the purview of one of ordinary skill in the art, there are at least four processing parameters that are important to make a coating with optimal uniformity and particulate release while maintaining adequate drug transfer and retention.

The parameters of the coating process include: (1) balloon conditioning; (2) balloon rotation rate; (3) coating solution flow rate; and (4) drying time. The interplay between each of the aforementioned parameters may be modified to enhance the optimal drug delivery, while reducing large particulate concentrations and providing a high level of drug retention on the balloon surface until delivery to a vessel wall.

Parameter selection is based on making a coating having the following characteristics: (1) uniform coating; (2) low particulate levels; and (3) a conformal coating. A uniform coating would include about +/−15% variation along the length and around the circumference of the balloon. In a preferred embodiment, uniformity with variations of no more than about +/−10% along the length and around the circumference of the balloon should be the goal. Particulates, defined as 10 μm in diameter or larger, in relatively low levels is highly preferred. Low particulate levels having a range of less than 30 particulates/mm$^2$ of coated balloon surface is within the scope of the invention, but a preferred coating would release less than 15 particulates/mm$^2$. Conformal coating with a thickness ranging from 2 to 20 μm is preferred, but thickness ranges between 5-15 μm is highly preferred.

The step of balloon preconditioning of a drug coated balloon allows the coating to contour the surface of the balloon without leaving areas that are non-coated. This conditioning cycle results in a freshly cleaned surface that is "primed" for a homogenous conformal coating having the desired drug loading uniformly distributed along the length and around the circumference of the balloon having a low particulate count.

In an example method of manufacture, a two-stage pre-conditioning cycle is utilized. The first step includes a 5 minutes ultra-sonication while submerged in a pre-conditioning solution that includes acetone and ethanol (e.g., 90% acetone/10% ethanol solution). A second stage is a repeat of the first stage, but in a "clean" or fresh batch of a pre-conditioning solution that includes acetone and ethanol (e.g., 90% acetone/10% ethanol solution). This embodiment provides for the conditioning parameters that are modifiable.

The following conditioning parameters are within the scope of the disclosure. Total conditioning time should comprise at least about 1 minute, but should not exceed more than about 20 minutes. In a preferred embodiment, the preconditioning time should be in a range from about 5-15 minutes. The acetone/ethanol solution will comprise a range of a minimum of about 70% and a maximum of about 95% acetone. In a preferred embodiment, acetone should be in a range from about 85-95%. Ethanol should be at a minimum of 5% and a maximum of 30% of the acetone/ethanol solution. Optimal ethanol concentrations will be about 5-15%.

In an exemplary method, a folded balloon catheter is immersed in a pre-conditioning solution, and pre-conditioning solution is at least partially dried on said balloon catheter. Subsequently, the pre-conditioned balloon catheter is partially expanded, and coated with a restenosis inhibitor.

Embodiments of the present disclosure include a metered injection process in which a predetermined amount of coating solution is applied to a folded balloon at one time, as described in U.S. Patent Publication No. 2011/0099789 published on May 5, 2011 filed on May 1, 2009. In one embodiment, an injection device, such as, for example and without limitation, a precision glass syringe, a pipette, a nozzle, etc., is filled with the exact amount of coating solution required to achieve the desired concentration of a therapeutic on the balloon. If necessary, the injection device could be refilled from a reservoir and additional coating solution added. In an alternative, the concentration of the therapeutic in the coating solution is optimized. For examples using a syringe, the needle of the syringe is placed in close proximity to the balloon surface and the coating solution is applied to the balloon by depressing a plunger and moving the needle over the surface of the balloon to be coated. Once all required coating solution is applied to the balloon, the balloon is rotated for a short period of time to obtain a uniform distribution of coating solution over the coated surfaces and to allow the surface coating to partially dry.

Balloon rotation rate provides a method where the needle contours the surface of the balloon to evenly distribute the coating onto the surface of the balloon. In particular, the balloon is rotated between about 1 and about 6 revolutions per second. In a more preferred embodiment the rotation rate would be between about 3.3 and about 3.7 revolutions per second.

In this examplary embodiment, coating solution flow rate is from 0.2 μl/sec to 6 μl/sec (and in certain embodiments, 1 μl/sec to 6 μl/sec). Optimal flow rate is between about 2.85 and 5.8 μl/sec based on the diameter of the balloon. The flow rate is a function of the coating solution volume, balloon diameter, and the x-axis travel speed. In a preferred embodiment, the x-axis velocity is between about 3 and 6 mm/sec. In a more preferred embodiment, the x-axis travel speed is about 4.5 and 5.3 mm/sec. Table 1 provides a non-exhaustive list of examples of balloon diameter, x-axis needle velocity and dispense rates and the interplay between each variable.

The drying time is important to the final product since this parameter impacts the coating's integrity during the final sheathing process. One observation in drying parameters is the balance between coating wetness and dryness. If the coating is too dry, it can cause the coating to flake. Conversely, if the coating is not dried sufficiently, the coating will scrape off of the balloon. In a preferred embodiment, drying times range from 160 to 200 seconds with a temperature from 60° F. to 76° F., and a relative humidity of from 39% to 56%. In another related embodiment, a drying time of 170 seconds to 190 seconds under the same clean room conditions is employed.

TABLE 1

| Flow rate parameters | | |
|---|---|---|
| Balloon Diameter (mm) | X-axis needle velocity (mm/sec) | Dispense rate (μl/sec) |
| 4 | Constant at 4.55 mm/sec | 2.85 |
| 5 | | 3.57 |
| 6 | | 4.28 |
| 7 | | 5.00 |

Balloons prepared by methods described herein can be used in methods of treatment. In certain embodiments, the present disclosure provides a method of treating a vessel wall comprising: positioning a balloon catheter in a stenosed vessel within a body vessel, said balloon catheter having a restenosis inhibitor on a substantial portion of the external surface; inflating said balloon catheter to an expanded configuration, wherein the vessel wall being in physical communication with a substantial portion of the external surface of said balloon catheter when inflated; transferring a restenosis inhibitor to said vessel wall; and preferably maintaining contact of said balloon catheter with said vessel wall for a time sufficient to deliver a therapeutically effective amount of restenosis inhibitor to said treatment site within said body vessel.

Exemplary Embodiments

1. A method of making a balloon catheter, the method comprising:

providing a balloon catheter comprising a catheter having a balloon coupled to one end of the catheter, wherein the balloon has an external surface, a length, and a circumference;

providing a coating solution comprising:
30 mg/ml to 90 mg/ml paclitaxel;
at least 45 mg/ml iopromide (and typically no more than 450 mg/ml);
7.5 vol-% to 50 vol-% acetone;
30 vol-% to 80 vol-% ethanol; and
at least 4 vol-% water (or at least 10 vol-%, and typically no more than 40 vol-% water);
coating the balloon with the coating solution and drying the coating solution on the balloon to provide a balloon catheter having a dried coating on the external surface of the balloon.

2. The method of embodiment 1 wherein the balloon catheter comprises paclitaxel at a concentration of 3 μg/mm² on the external surface of the balloon.

3. The method of embodiment 1 or 2 wherein the dried coating is a uniform coating with +/−15% (and in certain embodiments, +/−10%) variation along the length and around the circumference of the balloon.

4. The method of any of embodiments 1 through 3 wherein the dried coating is a conformal coating with a thickness ranging from 2 μm to 20 μm (and in certain embodiments, 5 μm to 15 μm).

5. The method of any of embodiments 1 through 4 wherein the dried coated balloon releases less than 30 particulates of the dried coating (which can include paclitaxel and iopromide) per mm² of the balloon surface during expansion of the coated balloon (as counted using the Particle Counting Method described herein).

6. The method of any of embodiments 1 through 5 wherein coating the balloon comprises applying a predetermined amount of the coating solution while the balloon is rotated at a rate of 1 to 6 revolutions per second (in some embodiments, at a rate of 3.3 to 3.7 revolutions per second).

7. The method of any of embodiments 1 through 6 wherein coating the balloon comprises applying a predetermined amount of the coating solution at a flow rate of 0.2 μl/sec to 6 μl/sec (and often 1 μl/sec to 6 μl/sec, and in certain embodiments 2.85 to 5.8 μl/sec).

8. The method of any of embodiments 1 through 7 wherein coating the balloon comprises coating the balloon with a first and a second layer of the coating solution (typically, without drying the first layer before applying the second layer).

9. The method of any of embodiments 1 through 8 wherein the balloon is folded and partially expanded prior to coating the balloon with the coating solution.

10. A method of coating a folded balloon catheter, the method comprising:
providing a balloon catheter comprising a catheter having a folded balloon coupled to one end of the catheter, wherein the balloon has an external surface, a length, and a circumference;
immersing the folded balloon in a pre-conditioning solution;
at least partially drying the pre-conditioning solution on the balloon to form a pre-conditioned balloon;
partially expanding the pre-conditioned balloon; and
coating the external surface of the pre-conditioned balloon with a restenosis inhibitor.

11. The method of embodiment 10 wherein the restenosis inhibitor comprises an active agent (i.e., therapeutic agent) and a contrast agent.

12. The method of embodiment 11 wherein the active agent is paclitaxel and the contrast agent is iopromide.

13. The method of embodiment 12 wherein coating the external surface of the pre-conditioned balloon with a restenosis inhibitor comprises:

providing a coating solution comprising:
30 mg/ml to 90 mg/ml paclitaxel;
at least 45 mg/ml iopromide (and typically no more than 450 mg/ml);
7.5 vol-% to 50 vol-% acetone;
30 vol-% to 80 vol-% ethanol; and
at least 4 vol-% water (or at least 10 vol-%, and typically no more than 40 vol-%); and
coating the balloon with the coating solution and drying the coating solution on the balloon under conditions effective to provide a balloon catheter having a dried coating on the external surface of the balloon.

14. The method of any of embodiments 10 through 13 wherein the pre-conditioning solution comprises acetone and ethanol.

15. The method of embodiment 14 wherein the pre-conditioning solution comprises 70% to 95% acetone and 5% to 30% ethanol.

16. The method of any of embodiments 10 through 15 wherein immersing the balloon in a pre-conditioning solution comprises subjecting the balloon to ultra-sonication while submerged in a pre-conditioning solution for 1 minute to 20 minutes.

17. A method of coating a balloon catheter comprising:
providing a balloon catheter comprising a catheter having a folded balloon coupled to one end of the catheter;
subjecting the folded balloon to a pre-conditioning cycle to form a pre-conditioned balloon;
partially inflating the balloon (e.g., by applying 3 psi pressure) to provide a uniform coating on the balloon with preservation of the balloon's capability of being reproducibly refolded;
coating the pre-conditioned and partially inflated balloon with a coating solution comprising a restenosis inhibitor;
wherein the coating step comprises applying a predetermined amount of the coating solution at a flow rate of 0.2 μl/sec to 6 μl/sec (and often 1 μl/sec to 6 μl/sec) while the balloon is being rotated; and
drying the coating solution to form a dried coated balloon coupled to the catheter, wherein the dried coating comprises the restenosis inhibitor.

18. The method of embodiment 17 further comprising inserting the coated balloon into one or more sheaths to aid in refolding the balloon.

19. The method of embodiment 18 wherein inserting the coated balloon into one or more sheaths comprises:
deflating the balloon to 0 psi from the state of partial inflation (e.g., typically at 3 psi);
inserting the coated deflated balloon into a first sheath (typically, the first sheath is applied to a balloon that is at least partially dried);
applying a vacuum (e.g., −5 psi) to the balloon;
removing the first sheath; and
inserting the coated balloon into a second final sheath;
wherein the first sheath has a diameter 5% to 15% larger than the diameter of the final sheath.

20. The method of any of embodiments 17 through 19 wherein the restenosis inhibitor comprises paclitaxel and iopromide.

21. The method of embodiment 20 wherein the coating solution comprises paclitaxel and iopromide in amounts such that a weight ratio of paclitaxel to iopromide (P:I) is less than 0.8:1 (and in certain embodiments, 0.1:1 to 0.8:1).

22. The method of any of embodiments 17 through 21 wherein the coating solution comprises acetone and ethanol in amounts such that a volume ratio of acetone to ethanol (A:E) is from 0.5:1 to 5:1.

23. The method of any of embodiments 17 through 22 wherein the coating solution comprises:
  30 mg/ml to 90 mg/ml paclitaxel;
  at least 45 mg/ml iopromide (and typically no more than 450 mg/ml);
  7.5 vol-% to 50 vol-% acetone;
  30 vol-% to 80 vol-% ethanol; and
  at least 4 vol-% water (or at least 10 vol-%, and typically no more than 40 vol-% water).

24. The method of embodiment 23 wherein the coating solution is prepared by a method comprising:
  dissolving paclitaxel in ethanol and acetone to form a paclitaxel solution;
  providing an aqueous solution comprising the iopromide dissolved in the water;
  adding the aqueous iopromide solution to the paclitaxel solution to form a restenosis inhibitor solution; and
  adding the acetone to the restenosis inhibitor solution to form a final coating solution.

25. A balloon catheter prepared by the method of any of embodiments 1 through 9.

26. A balloon catheter prepared by the method of any of embodiments 10 through 16.

27. A balloon catheter prepared by the method of any of embodiments 17 through 24.

28. A balloon catheter comprising a catheter having a balloon coupled to one end of the catheter, wherein the balloon has an external surface, a length, and a circumference;
  wherein the external surface of the balloon is coated with a dried coating comprising a restenosis inhibitor;
  wherein the coating is a uniform coating with +/−15% variation (in certain embodiments, +/−10% variation) along the length and around the circumference of the balloon;
  wherein the coating is a conformal coating with a thickness ranging from 2 μm to 20 μm (in certain embodiments, 5 μm to 15 μm); and
  wherein the dried coated balloon releases less than 30 particulates of the dried coating per mm$^2$ of the balloon surface during expansion of the coated balloon.

29. The balloon catheter of embodiment 28 wherein the restenosis inhibitor comprises paclitaxel and iopromide.

30. The balloon catheter of embodiment 29 wherein the weight ratio of paclitaxel to iopromide in the dried coating is less than 0.8:1.

31. A method of treating a vessel wall comprising:
  positioning a balloon catheter of embodiment 25 in a stenosed vessel of a subject;
  inflating the balloon of the balloon catheter to an expanded configuration, wherein the vessel wall of the stenosed vessel is in physical communication with a substantial portion of the external surface of the balloon when inflated; and
  transferring paclitaxel and iopromide to the vessel wall from the external surface of the balloon.

32. A method of treating a vessel wall comprising:
  positioning a balloon catheter of embodiment 26 in a stenosed vessel of a subject;
  inflating the balloon of the balloon catheter to an expanded configuration, wherein the vessel wall of the stenosed vessel is in physical communication with a substantial portion of the external surface of the balloon when inflated;
  transferring a restenosis inhibitor to the vessel wall from the external surface of the balloon; and
  maintaining contact between the external surface of the balloon and the vessel wall for a time sufficient to deliver a therapeutically effective amount of the restenosis inhibitor to a treatment site of the stenosed vessel.

33. A method of treating a vessel wall comprising:
  positioning a balloon catheter of embodiment 27 in a stenosed vessel of a subject;
  inflating the balloon of the balloon catheter to an expanded configuration, wherein the vessel wall of the stenosed vessel is in physical communication with a substantial portion of the external surface of the balloon when inflated;
  transferring a restenosis inhibitor to the vessel wall from the external surface of the balloon. and
  maintaining contact between the external surface of the balloon and the vessel wall for a time sufficient to deliver a therapeutically effective amount of the restenosis inhibitor to a treatment site of the stenosed vessel.

34. A method of treating a vessel wall comprising:
  positioning a balloon catheter of embodiment 28 in a stenosed vessel of a subject;
  inflating the balloon of the balloon catheter to an expanded configuration, wherein the vessel wall of the stenosed vessel is in physical communication with a substantial portion of the external surface of the balloon when inflated;
  transferring a restenosis inhibitor to the vessel wall from the external surface of the balloon; and
  maintaining contact between the external surface of the balloon and the vessel wall for a time sufficient to deliver a therapeutically effective amount of the restenosis inhibitor to a treatment site of the stenosed vessel.

35. A method of making a balloon catheter coating for delivery of a restenosis inhibitor comprising:
  combining paclitaxel and acetone making an active agent, wherein a final active agent comprises 30 mg/ml to 90 mg/ml paclitaxel and 7.5% to 50% acetone; and
  combining a contrast media and ethanol making a contrast media solution, wherein said contrast media solution initially having concentrations of about 10% to about 30% contrast media solution and a final contrast media having about 30% to about 80% ethanol,
  combining said contrast media solution and said active agent, wherein said contrast media solution and said active agent making a restenosis inhibitor,
  wherein said restenosis inhibitor being a substantial portion of the balloon catheter coating being at least 450 mg/ml iopromide and at least 40% water and the balloon catheter coating being in solution providing a uniform coating on the external surface of the balloon catheter in a concentration of about 3 μg/mm$^2$.

36. A coated medical device comprising:
  a catheter, extending along a longitudinal axis and having a first end and a second end and having at least one lumen;
  a balloon coupled to said first end or said second end;
  a coating for delivery of a restenosis inhibitor,
  wherein said coating being in solution providing a uniform coating on the external surface of a balloon catheter in a concentration of about 3 μg/mm$^2$ and said coating having 7.5% to 50% acetone and 30% to 80% ethanol as a means to get a restenosis inhibitor in solution, whereby said restenosis inhibitor contains at least 30 mg/ml to 90 mg/ml Paciltaxel and 10% to 30% contrast media solution, wherein said solution being at least 450 mg/ml iopromide and at least 40% water.

37. A method of coating a folded balloon catheter comprising:
   providing a folded balloon catheter;
   immersing said folded balloon catheter in a preconditioning solution;
   at least partially drying said pre-conditioning solution on said balloon catheter;
   at least partially expanding said balloon catheter; and
   coating a pre-conditioned balloon catheter surface with a restenosis inhibitor.

38. A method of treating a vessel wall comprising:
   positioning a balloon catheter in a stenosed vessel within a body vessel, said balloon catheter having a restenosis inhibitor on a substantial portion of the external surface;
   inflating said balloon catheter to an expanded configuration, wherein the vessel wall being in physical communication with a substantial portion of the external surface of said balloon catheter when inflated;
   transferring a restenosis inhibitor to said vessel wall, wherein said balloon catheter having a restenosis inhibitor agent coated on the balloon with uniformity of at least 10% along the length and around the circumference, the particulates of said restenosis inhibitor being at least 10 μm or larger in diameter and being less than 30 particulates/mm² of surface of said balloon catheter; and maintaining contact of said balloon catheter with said vessel wall for a time sufficient to deliver a therapeutically effective amount of restenosis inhibitor to said treatment site within said body vessel.

Examples

The coated balloon catheter was validated in pre-clinical and bench studies. The contents described herein provide for a detailed description of the project definitions, measurement processes and general experimental outcomes. The initial drug delivery measures the amount of drug transferred to the target lesion. Three separate study methods being employed help to distinguish between different coated balloon products.

Ex-vivo drug transfer studies were utilized. Bench studies using flowing water set to 37° C. and a latex tubing section represent the flowing vasculature system. The method quantitatively measures the amount of drug transferred to inner lumen of the latex tube, drug loss from introducer, amount of drug dissolved in the water, and relative number of particles released down-stream. This method serves as a comparative tool rather than a comprehensive evaluation of how the coating will perform clinically.

In another validation study, acute transfer (10 min) via SEM, was used. The drug coated balloon was applied to live rabbit right and left iliac. 10 minutes after the application, the rabbits were sacrificed and the target vessel was removed and staged for SEM analysis. The intent of this study was to qualitatively evaluate the amount, uniformity and morphology of the drug that was successfully transferred to the vessel wall.

In another related validation study, live rabbits were treated with the drug coated balloons and sacrificed at different time intervals (1 hr, 24 hr, 7 days, and/or 28 days). The endothelium layer and vessel walls were then extracted and analyzed for paclitaxel concentrations at the corresponding time-points. 1 hr is considered a measure of the initial drug transfer, whereas the later time points profiles the drug retention over time.

Drug load was measured by extracting balloons and analyzing the extraction solvent using HPLC methodology for paclitaxel and iopromide concentration. In addition, the same method was also capable of measuring impurity levels from the same sample. Both drug content and impurities were evaluated over the course of the development cycle.

Particle Counting Method

Two methods of submerge and deploy particulate counting were utilized during the coating development cycle. Initially, the particle counts were obtained using a closed loop flowing water system and flow through cell with light obscuration particle detection. The method is considered a conservative approach that exposes the balloon to a flowing system while being deployed, but the method is found to have significant variability. This custom made apparatus was considered to be sufficient for comparison of the development coatings. Additionally, a Beckman Coulter Accusizer 4 particle analyzer can be used for verification. This new method provided the analyst more consistent sample handling as well as more reliable data.

In a typical method, coated balloon catheters with the stabilizing mandrel wire inside of their lumen were placed in test vessel with Isoton II solution and immediately inflated using Z-Axis apparatus to a pressure of 8000 mbar. The catheters were kept to 60 seconds and then deflated to −800 mbar for 3 seconds and removed from the Isoton II solution. Contents of inflation vessel was immediately placed into a labeled Multisizer 4 particle counter machine and number of particles with different sized was automatically counted.

Uniformity

The uniformity of the coating on the balloon is measured in two directions; longitudinally (along the length) and circumferentially (around the circumference). Although the longitudinal uniformity test method is well understood, a circumferential uniformity test method provides a more thorough analysis of the overall uniformity of the coating process.

Longitudinal Uniformity Test Method

The purpose of this test method is to measure the distribution of drug along the along the length of the drug eluting balloon. To determine the longitudinal uniformity, samples are sectioned into three segments along the length of the balloon. Each segment was then measured with a caliper to determine its true length. All of the segments were then extracted with 90% ethanol solution in water and analyzed using a state of the art HPLC to determine the drug and excipient content. The resulting values were then normalized by the corresponding segment length to determine the component concentration per unit length.

Circumferential Uniformity Test Method

The purpose of this test method is to measure the distribution of drug around the circumference of the drug eluting balloon. The process of measuring the coating around the circumference of the balloon requires the use of an adhesive tape wrapped tightly around a fully inflated balloon. The adhesive from the tape readily dissolves from the coating during the extraction process. This technique allows the middle section of the balloon to be cut along its length into three separate segments. All resulting segments are then extracted with 90% ethanol solution in water and analyzed using a state of the art HPLC to determine the corresponding drug and excipient content. After the extraction process, the remaining balloon material from each of the extracted segments are rinsed and dried to obtain the balloon material weight which was used as the normalization factor A non-exhaustive list of drug-coated balloon characteristics are shown in Table 2b. The characteristics of the coating solution and parameters of coating are in Table 2a. Five of the solutions tested met the coating design criteria (reduced particulate count (average of three balloons), uniform coating distribution, and some signs of crystallinity).

TABLE 2A

Coating properties resulting from analysis of development coatings

|  | 0.4 w/ stripes (0.5 rps rotation rate) | 0.4 w/o stripes (1.0 rps rotation rate) | 0.8 - 80/20 60/40 (A/E ratio) | 0.8 - (A/E ratio) | 0.4 Dual layer |
|---|---|---|---|---|---|
| Drug loading | 3 µg/mm$^2$ | 3 µg/mm$^2$ | 3 µg/mm$^2$ | 3 µg/mm$^2$ | 3 µg/mm$^2$ |
| PTX | 60 mg/ml | 60 mg/ml | 90 mg/ml | 90 mg/ml | 60 mg/ml |
| P/I, g/g | 0.4 | 0.4 | 0.8 | 0.8 | 0.4 |
| A/E, v/v | 1.3 | 1.3 | 1.5 | 4.0 | 1.3 |
| Rps | 0.5 | 1.0 | 1.0 | 1.0 | 1.0 |
| Flow, µl/s | 1.1 | 1.1 | 1.1 | 1.1 | 0.8 |
| Nylon-12 Balloon size | 6 mm × 80 mm | 6 × 80 | 6 × 80 | 6 × 80 | 6 × 80 |

TABLE 2B

Coating properties resulting from analysis of development coatings

|  | 0.4 w/ stripes (0.5 rps rotation rate) | 0.4 w/o stripes (1.0 rps rotation rate) | 0.8 - 60/40 (A/E ratio) | 0.8 - 80/20 (A/E ratio) | 0.4 Dual layer |
|---|---|---|---|---|---|
| Drug loading | 3 µg/mm$^2$ | 3 µg/mm$^2$ | 3 µg/mm$^2$ | 3 µg/mm$^2$ | 3 µg/mm$^2$ |
| Particulate >10 µm | 22,000 | 22,000 | 10,600 | 16,000 | 12,500 |
| Ave and max | 26,000 | 29,000 | 14,000 | 26,000 | 14,000 |
| Particulate >50 µm | 3800 | 1600 | 1700 | 1,200 | 2800 |
| Ave and max | 6900 | 2500 | 2300 | 1500 | 3800 |
| Particulate >100 µm | 190 | 50 | 46 | 34 | 180 |
| Ave and max | 220 | 73 | 69 | 53 | 260 |
| Circumferential Uniformity | 19/22-10% 23/24-15% 16% max | 13/20-10% 17/20-15% 22% max | 22/24-10% 23/24-15% 18% max | 16/24-10% 21/24-15% 19% max | 20/22-10% 21/24-15% 17% max |
| Longitudinal Uniformity | 6/8-10% 12% max | 6/8-10% 16% max | 7/8-10% 11% max | 7/8-10% 11% max | 8/8-10% 4% max |
| Crystallinity | Mostly amorphous | Mostly amorphous | Mostly amorphous | Mostly amorphous | Sub-layer appears Crystalline |

Ex-Vivo Drug Transfer Study

An ex-vivo loop is used to simulate the fluid dynamics of a peripheral arterial vascular system by circulating water in a fluid loop at 37° C. at 300 ml/min and 60 mmHg (1.5 psi). A drug coated balloon is inserted into a hemostasis valve introducer allowing contact between the hemostasis valve and the drug coating during insertion. After introduction, the balloon is exposed to flowing water for 30 seconds to simulate travel time thru the vascular system in a clinical procedure. The balloon is then inflated to 8 atm for 1 min against flexible silicone rubber tubing after which it is deflated and flow continued for another 30 seconds. The balloon is then removed from the fluid without retraction through the introducer. Balloon residual drug (paclitaxel) content is measured with HPLC (this is denoted as "balloon" in Table 3). Drug remaining on the silicone rubber is denoted as "Tubing" in Table 3. Finally, two rows denoted as ">100 µm" and "100-10 µm" in Table 3 refer to the amount of drug recovered from filtering water solution used for ex-vivo loop set up with 100 µm pore size and 10 µm pore size (applied after filtering with 100 µm filter), respectively.

Table 3 shows both coating P/I ratios (paclitaxel to iopromide) (0.4 and 0.8) tested for drug transfer and downstream particulate levels via ex-vivo analysis to determine which coating solution would be evaluated. The ex-vivo results suggested the drug transfer was higher for the 0.4P/I as opposed to the 0.8P/I ratio coating. The drug load applied using a 0.4P/I ratio coating solution was limited to 2 µg/mm$^2$ of the coating solution. The volume of coating solution applied to the balloon could be increased to achieve the 3 µg/mm$^2$ with a 60 mg/ml paclitaxel concentration. However, to accomplish this, the final sheath size required will be slightly larger and the drying time needed increasing to allow for the solvents to flash off.

TABLE 3

Ex-vivo results from testing 0.4 and 0.8 P/I ratio coatings

| Location | 0.4 P/I at 2 µg/mm$^2$ RT Dry | 0.8 P/I at 3 µg/mm$^2$ RT Dry |
|---|---|---|
| Balloon | 17.04% | 34.49% |
| >100 µm | 6.23% | 8.33% |

TABLE 3-continued

Ex-vivo results from testing 0.4 and 0.8 P/I ratio coatings

| Location | 0.4 P/I at 2 µg/mm$^2$ RT Dry | 0.8 P/I at 3 µg/mm$^2$ RT Dry |
|---|---|---|
| 100-10 µm | 7.04% | 8.76% |
| Tubing | 56.95% | 33.38% |

Figure 2:
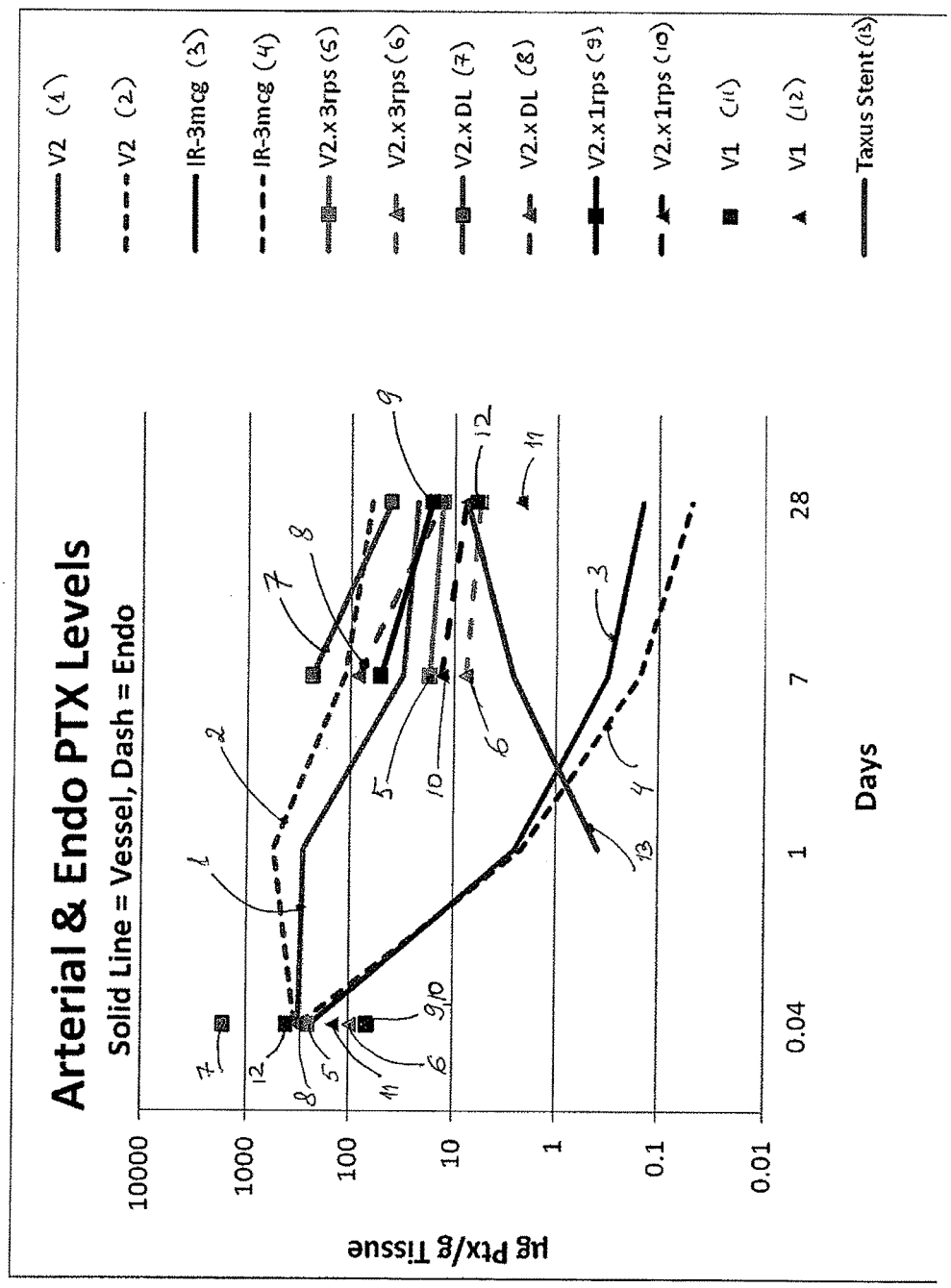
FIG. 2 is a graph of paclitaxel levels.

FIG. 2 summarizes various coating embodiments evaluated at the animal model level. Within the data sets, a Dual layer coating embodiment is designated as V2.x DL and single layer coatings are identified as V2.x 3 rps and V2.x 1 rps (two separate rotation rates were evaluated on the single layer to alleviate concerns regarding the effect of minor processing changes. The plot suggests that the 0.4P/I dual layer coating may transfer significant more drug and have improved retention over time than all other coatings evaluated. The single layer coatings resulted in less transfer, but nearly equivalent retention as the V1 product and better retention than other development coatings (IR-3 mcg). In addition, the level of Paclitaxel in the tissue at 28 days is comparable to the Taxus drug eluting stent.

Examples of Coating Procedures for FIG. 2 Graph.
1. V2.x1 rps coating procedure.
   a. Solution preparation
      i. Weigh out paclitaxel (6000.0 mg);
      ii. Add 40 ml of Acetone and dissolve paclitaxel;
      iii. Using a Harvard Twin Syringe Pump, add 32.5 ml ethanol to the paclitaxel in acetone;
      iv. Sonicate the mixture for 10 minutes until solution is homogeneous and clear;
      v. Using the syringe pump, add ULTRAVIST 370 (20.0 ml), which includes iopromide, water, and a preservative, to the solution of paclitaxel in acetone/ethanol mix;
      vi. Sonicate for 5 min until solution is clear;
      vii. Bring solution to room temperature;
      viii. Bring the solution to volume (100 ml) with acetone;
      ix. Thus "final" coating solution includes 154 mg/ml of iopromide.
   b. Catheter Pre-conditioning procedure
      i. Place catheter in 9:1 v/v solution of Acetone/Ethanol for 10 min;
      ii. Remove catheter and place it in the fresh 9:1 v/v solution of Acetone/Ethanol for additional 10 min.
      iii. Dry catheters at ambient conditions for not less than 10 min, but not longer than 5 h.
   c. Catheter coating procedure
      i. Place 6 mm by 80 mm balloon catheter in the coating apparatus and put minimum tension on the catheter shaft to keep balloon visually straight.
      ii. Partially inflate balloon to 3 psi;
      iii. Initiate coating process with following parameters: coating solution flow rate 1.1 µl/s, balloon rotation speed of 1 rps, and total coating solution dispense volume to 75.4 µl (this provides coating at 3 µg/mm$^2$ level).
      iv. After completion of coating dispense process, leave balloon rotating at 1 rps speed for additional 90 second to allow further drying
      v. Stop catheter rotation and deflate balloon to ambient pressure.
      vi. Place the PTFE flared tubing (pre-sheath with 5% to 15% larger diameter that the final sheath) tubing on the balloon to pre-fold it
      vii. Further deflate balloon to −5 psi
      viii. Remove pre-sheath and put final sheath of the balloon surface
2. V2.x3 rps coating procedure.
   a. Same as in about Example 1 with exception of balloon rotation speed (during coating and drying steps) of 3 rps vs 1 rps used in the Example 1
3. IR-3 mcg coating procedure.
   a. Same as in about Example 1 with the exception of the drying conditions, as shown below in description of catheter coating procedure
      i. Place 6 mm by 80 mm balloon catheter in the coating apparatus and put minimum tension on the catheter shaft to keep balloon visually straight.
      ii. Partially inflate balloon to 3 psi;
      iii. Initiate coating process with following parameters: coating solution flow rate 1.1 µl/s, balloon rotation speed of 1 rps, and total coating solution dispense volume to 75.4 µl (this provides coating at 3 µg/mm$^2$ level).
      iv. While dispensing coating solution on the rotating balloon surface apply heat from the IR source (500 W). After end of coating solution dispensing continue to rotate balloon for additional 30 s while applying heat from IR source.
      v. Remove heat, stop catheter rotation and deflate balloon to ambient pressure.
      vi. Place the PTFE flared tubing (pre-sheath with 5% to 15% larger diameter that the final sheath) tubing on the balloon to pre-fold it
      vii. Further deflate balloon to −5 psi
      viii. Remove pre-sheath and put final sheath of the balloon surface
4. V2.x DL coating procedure.
   a. Solution preparation is the same as in Example 1.
   b. Coating procedure
      i. Place 6 mm by 80 mm balloon catheter in the coating apparatus and put minimum tension on the catheter shaft to keep balloon visually straight.
      ii. Partially inflate balloon to 3 psi;
      iii. Initiate coating process with following parameters: coating solution flow rate 0.8 µl/s, balloon rotation speed of 1 rps, and total coating solution dispense volume to 75.4 µl (this provides coating at 3 µg/mm$^2$ level).
      iv. Balloon is coated in two steps: Firstly, 37.7 µl of coating solution is dispensed uniformly on the balloon at the rate of 0.8 µl/s. Secondly, remaining 37.7 µl of coating solution is evenly dispersed on the pre-coated balloon surface at the rate of 0.8 µl/s. The dwell time between the end of the first coating step and the beginning of the second coating step is 10 seconds.
      v. After completion of the second coating step, leave balloon rotating at 1 rps speed for additional 90 second to allow further drying
      vi. Stop catheter rotation and deflate balloon to ambient pressure.
      vii. Place the PTFE flared tubing (pre-sheath with 5% to 15% larger diameter that the final sheath) tubing on the balloon to pre-fold it
      viii. Further deflate balloon to −5 psi
      ix. Remove pre-sheath and put final sheath of the balloon surface
5. V2 coating procedure.
   a. Solution preparation
      i. Weigh out paclitaxel (9000.0 mg);
      ii. Add 60 ml of Acetone and dissolve paclitaxel;
      iii. Using a Harvard Twin Syringe Pump, add 32.5 ml ethanol to the paclitaxel in acetone;
      iv. Sonicate the mixture for 10 minutes until solution is homogeneous and clear;
      v. Using the syringe pump, add ULTRAVIST 370 (7.5 ml), which includes iopromide, water, and a preservative, to the solution of paclitaxel in acetone/ethanol mix;
      vi. Sonicate for 5 min until solution is clear;
      vii. Bring solution to room temperature;
      viii. Bring the solution to volume (100 ml) with acetone;
      ix. Thus "final" coating solution includes 57.7 mg/ml of iopromide.
   b. Catheter Pre-conditioning procedure
      i. Place catheter in 9:1 v/v solution of Acetone/Ethanol for 10 min;
      ii. Dry catheters at ambient conditions c. Catheter coating procedure
  i. Place 6 mm by 80 mm balloon catheter in the coating apparatus and put minimum tension on the catheter shaft to keep balloon visually straight.
  ii. Initiate coating process with following parameters: coating solution flow rate 3.5 μl/s, total coating solution dispense volume to 50.2 μl (this provides coating at 3 μg/mm² level). Approximately 80% of total coating solution volume is evenly dispersed in all folds of the folded catheter. Remaining 20% of the total coating solution is evenly dispersed on the balloon catheter rotating at 3 rpm speed.
  iii. After completion of coating dispense process, leave balloon rotating at 3 rps speed for additional 50 second to allow further drying.
  iv. Stop catheter rotation and put final sheath of the balloon surface
6. V1 coating procedure.
  a. Solution preparation
    i. Weigh out paclitaxel (3000.0 mg);
    ii. Add 89 ml of Acetone and dissolve paclitaxel;
    iii. Add 9 ml Ethanol, carefully mix until solution is clear
    iv. Add ULTRAVIST 370 (2.0 ml) to the solution of paclitaxel in acetone/ethanol mix;
    v. Bring the solution to volume (100 ml) with acetone;
    vi. Thus "final" coating solution includes 15.4 mg/ml of iopromide.
  a. Catheter coating procedure
    i. Place 6 mm by 80 mm balloon catheter in the automatic dipping coating apparatus.
    ii. Perform full immersion of a folded balloon in a coating solution for 1 minute with a 4 hour drying time.
    iii. Perform three additional immersions of the pre-coated balloon, each for 15 seconds with a 1 hour intermediate drying time.

Table 4 below shows a particulate release profiles from testing large single and dual layer balloons.

coating properties for the following high level design inputs; reduced particles released and more preferred manufacturing process. It is also important to note that the drug loading of 3 μg/mm² is based on the surface area calculated by using the nominal length and diameter of the balloon to calculate surface area (e.g., S.A.=3.5×20×π for a 3.5×20 mm balloon). (A=best; B=intermediate; C=worst).

TABLE 5

Resulting ratings of single vs. dual layer coatings

| Parameter | V2.x1rps | V2.xDL | V2 |
|---|---|---|---|
| Uniformity | A | A | C |
| Particulate | A | B-C* | C |
| Ease of Manufacture/Manufacturing Consistency | A | B-C* | A |
| Drug Tissue Uptake | A | A | A |
| Drug Tissue Retention | B | A | A |
| Efficacy Signal | B | B | A |

The complete disclosures of the patents, patent documents, and publications cited herein are incorporated by reference in their entirety as if each were individually incorporated. While the various embodiments of the invention have been described above in terms of specific embodiments, it is to be understood that the invention is not limited to these disclosed embodiments. Upon reading the teachings of this disclosure many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification.

TABLE 4

| Particle Min Dia. | Ex. 1 | Ex. 2 | Ex. 3 | Mean | Std. Dev | Min. | Max. |
|---|---|---|---|---|---|---|---|
| Run: 8/Aug. 31, 2011 Single layer | | | | | | | |
| 10 | 32576 | 45703 | 25857 | 34712 | 10094 | 25857 | 45703 |
| 25 | 9494 | 9494 | 6573 | 8520 | 1686 | 6573 | 9494 |
| 50 | 2278 | 2278 | 1858 | 2138 | 242 | 1858 | 2278 |
| 75 | 661 | 661 | 445 | 589 | 125 | 445 | 661 |
| 100 | 212 | 212 | 139 | 188 | 42 | 139 | 212 |
| 150 | 20 | 20 | 24 | 22 | 2 | 20 | 24 |
| 201 | 0 | 0 | 8 | 3 | 5 | 0 | 8 |
| Largest (μm) | 160 | 177 | 247 | 247 | 46 | 247 | 247 |
| Run: Aug. 25, 2011 Dual Layer | | | | | | | |
| 10 | 231697 | 623623 | 276178 | 377166 | 214593 | 231697 | 623623 |
| 25 | 48786 | 132344 | 55804 | 78978 | 46349 | 48786 | 132344 |
| 50 | 17457 | 39290 | 15216 | 23988 | 13299 | 15216 | 39290 |
| 75 | 8314 | 17073 | 6282 | 10556 | 5735 | 6282 | 17073 |
| 100 | 4102 | 7776 | 2780 | 4886 | 2589 | 2780 | 7776 |
| 150 | 849 | 1702 | 649 | 1067 | 559 | 649 | 1702 |
| 201 | 69 | 306 | 86 | 154 | 132 | 69 | 306 |
| Largest (μm) | 267 | 298 | 289 | 289 | 16 | 289 | 289 |

Based on the information provided in Table 5, the single layer 0.4P/I ratio coating using a 60 mg/ml concentrated solution and applying the appropriate volumes resulted in a 3 μg/mm² dosage. The single layer coating having preferred

We claim:

1. A method of coating a balloon catheter comprising:
providing a balloon catheter comprising a catheter having a folded balloon coupled to one end of the catheter;

subjecting the folded balloon to a pre-conditioning cycle to form a preconditioned balloon;
partially inflating the balloon;
coating the pre-conditioned and partially inflated balloon with a coating solution comprising a restenosis inhibitor, wherein the coating solution is prepared by a process comprising dissolving the paclitaxel in acetone, adding ethanol to the paclitaxel dissolved in acetone to produce a paclitaxel acetone/ethanol mix, and adding a mixture comprising iopromide and water to the paclitaxel acetone/ethanol mix;
wherein the coating step comprises applying a predetermined amount of the coating solution at a flow rate of 0.2 µl/sec to 6 µl/sec while the balloon is being rotated; and
drying the coating solution to form a dried coated balloon coupled to the catheter, wherein the dried coating comprises the restenosis inhibitor.

2. The method of claim 1 further comprising inserting the coated balloon into one or more sheaths to aid in refolding the balloon.

3. The method of claim 2 wherein inserting the coated balloon into one or more sheaths comprises:
deflating the balloon to 0 psi from the state of partial inflation;
inserting the coated deflated balloon into a first sheath;
applying a vacuum to the balloon;
removing the first sheath; and
inserting the coated balloon into a second final sheath;
wherein the first sheath has a diameter 5% to 15% larger than the diameter of the final sheath.

4. The method of claim 1 wherein the coating solution comprises paclitaxel and iopromide in amounts such that a weight ratio of paclitaxel to iopromide is less than 0.8:1.

5. The method of claim 1 wherein the coating solution comprises acetone and ethanol in amounts such that a volume ratio of acetone to ethanol is from 0.5:1 to 5:1.

6. The method of claim 1 wherein the coating solution comprises:
30 mg/ml to 90 mg/ml paclitaxel;
at least 45 mg/ml iopromide;
7.5 vol-% to 50 vol-% acetone;
30 vol-% to 80 vol-% ethanol; and
at least 4 vol-% water.

7. The method of claim 1 wherein the coating solution is prepared by a method comprising:
dissolving paclitaxel in ethanol and acetone to form a paclitaxel solution;
providing an aqueous solution comprising the iopromide dissolved in the water;
adding the aqueous iopromide solution to the paclitaxel solution to form a restenosis inhibitor solution; and
adding the acetone to the restenosis inhibitor solution to form a final coating solution comprising
30 mg/ml to 90 mg/ml paclitaxel;
at least 45 mg/ml iopromide;
7.5 vol-% to 50 vol-% acetone;
30 vol-% to 80 vol-% ethanol; and
at least 4 vol-% water.

8. A balloon catheter prepared by the method of claim 1.

9. A method of treating a vessel wall comprising:
positioning a balloon catheter of claim 8 in a stenosed vessel of a subject;
inflating the balloon of the balloon catheter to an expanded configuration, wherein the vessel wall of the stenosed vessel is in physical communication with a substantial portion of the external surface of the balloon when inflated;
transferring a restenosis inhibitor to the vessel wall from the external surface of the balloon; and
maintaining contact between the external surface of the balloon and the vessel wall for a time sufficient to deliver a therapeutically effective amount of the restenosis inhibitor to a treatment site of the stenosed vessel.

10. The method of claim 1, wherein the coating solution consists essentially of paclitaxel, iopromide, acetone, ethanol, water and, optionally, a preservative.

* * * * *